United States Patent [19]

Koikeda et al.

[11] Patent Number: 4,622,308

[45] Date of Patent: Nov. 11, 1986

[54] CATALYST FOR THE PRODUCTION OF HYDROCARBONS FROM THE SYNTHESIS GAS

[75] Inventors: Minoru Koikeda; Takashi Suzuki, both of Yokohama; Koutaro Munemura, Zama; Yoshihiko Nishimoto; Tetsuya Imai, both of Hiroshima, all of Japan

[73] Assignee: Research Association for Petroleum Alternatives Development, Tokyo, Japan

[21] Appl. No.: 680,244

[22] Filed: Dec. 11, 1984

Related U.S. Application Data

[63] Continuation-in-part of Ser. No. 376,216, May 7, 1982, abandoned.

[30] Foreign Application Priority Data

May 18, 1981 [JP] Japan .................................. 56-73448
Sep. 25, 1981 [JP] Japan .................................. 56-150597

[51] Int. Cl.[4] ......................... B01J 29/10; B01J 29/20

[52] U.S. Cl. ......................................... 502/66; 502/74; 518/721

[58] Field of Search .................... 252/455 Z; 518/721, 518/715; 502/66, 74

[56] References Cited

U.S. PATENT DOCUMENTS

| | | | |
|---|---|---|---|
| 4,086,262 | 4/1978 | Chang et al. | 252/455 Z |
| 4,131,568 | 12/1978 | Bartish | 252/455 Z |
| 4,157,338 | 6/1979 | Haag et al. | 252/455 Z |
| 4,207,208 | 6/1980 | Lucki et al. | 518/721 X |
| 4,269,783 | 5/1981 | Brennan et al. | 518/721 X |
| 4,279,830 | 6/1981 | Haag et al. | 518/721 X |
| 4,556,645 | 12/1985 | Coughlin et al. | 502/66 |
| 4,579,830 | 4/1986 | Coughlin | 502/66 |

*Primary Examiner*—Carl F. Dees
*Attorney, Agent, or Firm*—Wenderoth, Lind & Ponack

[57] ABSTRACT

An improved catalyst suitable for use in the production of hydrocarbons from the synthesis gas comprises an iron-containing Fischer-Tropsch catalyst, a zeolite and at least one metal selected from the group consisting of ruthenium, rhodium, platinum, palladium, iridium, cobalt and molybdenum. This catalyst gives a high CO conversion and hydrocarbons enriched with $C_5{}^+$ gasoline fraction.

15 Claims, No Drawings

CATALYST FOR THE PRODUCTION OF HYDROCARBONS FROM THE SYNTHESIS GAS

CROSS-REFERENCE TO RELATED APPLICATION

This application is a continuation-in-part of Ser. No. 376,216, filed May 7, 1982, now abandoned.

BACKGROUND OF THE INVENTION

1. Field of the Invention

This invention relates to a process for the production of hydrocarbons having a high quality and a boiling point range of gasoline from mixed gases of carbon monoxide and hydrogen (which will hereinafter be referred to as "synthesis gas") and a catalyst suitable for use in this conversion reaction.

2. Description of the Prior Art

The surroundings of petroleum playing the leading part of energy at present are very unstable and it has been feared that a "valley" of energy will come in the last half of 1980s to the 1990s due to deficiency of petroleum. To this end, it is required to practice economy in the consumption of petroleum in future and to use an alternative energy for petroleum such as coal, nuclear fuel, LNG, etc. In particular, it has lately been watched with keen interest to develop the technique of $C_1$-chemistry to make up for the short supply of gasoline, kerosene and gas oil which demands will relatively be expanded by producing from other carbon sources than petroleum, e.g. coal and natural gas which can be found in abundance in the world.

Methods of producing hydrocarbons from coal can be classified mainly into two methods: direct method by liquefaction of coal and indirect method through the synthesis gas, and a number or studies have hitherto been made concerning these two methods. The liquefaction of coal is generally carried out by subjecting coal to hydrogenation under a high pressure in the presence of a solvent to obtain gaseous or liquid hydrocarbons, but this method is still under development and unfavourable economically and the quality of the products is inferior to petroleum at present. On the other hand, the indirect method, which has already been put to practical use by SASOL in South Africa, consists in a method of converting a carbon source into hydrocarbons by making carbon monoxide and hydrogen in the presence of air, oxygen or steam and reacting in the presence of a Fischer-Tropsch catalyst. It is well known in the art that carbon sources such as coal, natural gas and asphalt which are hard to be converted directly into gasoline, kerosene or gas oil are converted into mixed gases of carbon monoxide and hydrogen by the gasification technique established as an industrial technique and that the thus resulting mixed gases are contacted in the presence of a suitable catalyst and converted into hydrocarbons. This has been conducted on a commercial basis, as set forth above.

For example, the Fischer-Tropsch process is known as a process for producing hydrocarbon mixtures from the synthesis gas in the presence of a catalyst based on iron, cobalt, nickel, ruthenium, thorium and rhodium. However, the use of this catalyst results in reaction products of hydrocarbons including paraffins and olefins, distributed widely from methane to wax, and of various oxygen-containing compounds including alcohols and ethers and thus it is impossible to obtain selectively valuable products with a specified boiling point range. That is, the yield of the most valuable gasoline fraction is not sufficient and the gasoline fraction is not usable as motor gasoline as it is and should be modified, for example, by catalytic reforming, since it contains little aromatic hydrocarbons or highly branched parrafins or olefins and has low octane number.

Iron catalysts used on a commercial scale as a Fischer-Tropsch catalyst comprise a precipitated catalyst and fused catalyst, to which copper or potassium is added to raise the selectively thereof. These catalysts are effective for increasing waxes in the product, but do not serve to increase the yield of gasoline fraction and the octane number. On the other hand, ruthenium catalysts are excellent in the formation of high molecular weight waxes, but give only a low conversion of carbon monoxide unless the reaction pressure is kept more than 50 $kg/cm^2$ and produce liquid hydrocarbons enriched with n-paraffins whose estimation as gasoline is low. In addition, rhodium is known as a noble metal effective for the Fischer-Tropsch synthesis, but it results in a product consisting predominantly of oxygen-containing compounds in spite of its high activity. Other noble metals such as platinum, palladium and iridium have scarcely a catalytic activity according to some reports. Nickel is a methanation catalyst rather than the Fischer-Tropsch catalyst, since it has a very high conversion activity of carbon monoxide, but the resulting hydrocarbon is substantially methane.

Moreover, a two-stage process is known wherein the synthesis gas is contacted with a carbon monoxide reducing catalyst and the product is then contacted with a high silica zeolite catalyst of specified type charged in a same or different reactor, thus converting the synthesis gas into hydrocarbons containing mainly gasoline fraction with high octane number. The carbon nomoxide reducing catalyst used herein is a methanol synthesis catalyst containing two or more metals of copper, zinc and chromium or a Fischer-Tropsch synthesis catalyst of iron type consisting of precipitated iron or fused iron. The two-stage conversion process consists in producing gasoline fraction having high octane number in a high yield by converting once the synthesis gas into oxygen-containing compounds in the case of the methanol synthesis catalyst or converting the synthesis gas into hydrocarbons distributed widely from methane to waxes and oxygen-containing compounds in the case of the Fischer-Tropsch synthesis catalyst, and thereafter, contacting these products with a zeolite catalyst having a specified pore diameter.

Of late, processes for producing selectively hydrocarbons with a specified boiling point range from the synthesis gas by one stage have been found, one of which consists in using a catalyst obtained by mixing mechanically the carbon monoxide reducing catalyst and a specified zeolite used in the two-stage process (U.S. Pat. No. 4,086,262), and the other of which consists in using a catalyst obtained by supporting a carbon monoxide reducing metal or metal oxide on a specified zeolite (U.S. Pat. No. 4,157,338). In any process, the product is limited by the shape selectivity of a zeolite with specified pores as a consititutional component of the catalyst so that products having a larger molecular size than the pore diameter are hardly formed and hydrocarbons having a smaller molecular size and boiling point range of gasoline or less can selectively be obtained. The one-stage process is a more economical process than the two-stage process because of its simplified process.

However, the above described one-stage process using the mechanically mixed catalyst is inferior to the two-stage process because of the catalytic defects that the conversion of carbon monoxide and the yield of gasoline are low and there is formed a large amount of methane which is only estimated as a fuel gas. The other one-stage process using the catalyst obtained by supporting a metal capable of exhibiting a Fischer-Tropsch activity on a particular zeolite aims at subjecting the synthesis gas to a Fischer-Tropsch reaction by the metallic component in the catalytic composition to form a hydrocarbon mixture distributed from methane to waxes as an intermediate and then converting these hydrocarbons into hydrocarbons having a boiling point range of gasoline or less by the shape selectivity zeolite known to be effective for cracking waxes, i.e. ZSM-5 zeolite catalyst. The catalyst of this kind is prepared by impregnating ZSM-5 zeolite with iron or ruthenium as disclosed in Japanese Patent Application (OPI) No. 142502/1975. The former catalyst gives a relatively high conversion, but has the drawbacks that the conversion of carbon monoxide to carbon dioxide is increased resulting in decrease of the yield of $C_{5+}$ gasoline fraction and the resulting hydrocarbons consist predominantly of methane, while the latter catalyst gives a higher yield of $C_{5+}$ gasoline fraction than the former catalyst, but has the drawbacks on practical use that the activity is rapidly deteriorated with the passage of time and a higher reaction pressure, e.g. more than 50 $Kg/cm^2$ is required in order to obtain $C_{5+}$ gasoline fraction effectively. This catalyst is not useful because is loses the activity through heating at a temperature above 300° C. in an oxidizing atmosphere and thus it cannot be regenerated.

SUMMARY OF THE INVENTION

It is an object of the present invention to provide a catalyst for the production of hydrocarbons from the synthesis gas.

It is another object of the present invention to provide an improved catalyst of Fischer-Tropsch type.

It is a further object of the present invention to provide a process for the production of hydrocarbons from the synthesis gas using an improved catalyst of Fischer-Tropsch type.

These objects can be attained by a catalyst for the production of hydrocarbons from the synthesis gas, which comprises an iron-containing Fischer-Tropsch, catalyst, a zeolite and at least one metal selected from the group consisting of ruthenium, rhodium, platinum, palladium, iridium, cobalt and molybdenum, and by a process for the production of hydrocarbons from the synthesis gas using the catalyst.

DETAILED DESCRIPTION OF THE INVENTION

We, the inventors, have made various efforts to overcome the above described disadvantages and consequently have found that gasoline fraction with high octane number can be obtained from the synthesis gas in a high yield by the use of a catalyst prepared by adding at least one metal selected from the group consisting of ruthenium, rhodium, platinum, palladium, iridium, cobalt and molybdenum to a catalyst comprising an iron component known as a Fischer-Tropsch catalyst and a zeolite component. The present invention is based on this finding.

That is to say, the features of the present invention consist in a catalyst comprising at least one metal selected from the group consisting of ruthenium, rhodium, platinum, palladium, iridium, cobalt, and molybdenum supported on a composition of a zeolite and iron, and a process for producing hydrocarbons from the synthesis gas with unexpected merits from the prior art Fischer-Tropsch catalyst comprising a zeolite and iron or comprising ruthenium, cobalt, etc. In more detail, the specified metal such as ruthenium according to the present invention is added to iron and contacted with each other intimately, whereby to suppress markedly formation of methane which is formed in a large amount on an iron catalyst, to increase the yield of gasoline fraction containing aromatic hydrocarbons and branched paraffins or olefins and to suppress formation of carbon dioxide as a byproduct leading to the loss of carbon. Furthermore, the conversion of carbon monoxide is held sufficiently high even at a low reaction pressure, e.g. 10 to 20 $Kg/cm^2$. These advantages or merits are not obvious at all from a catalyst consisting of only ruthenium and the similar effects can be found when platinum, palladium and iridium that do not have the Fischer-Tropsch activity are added. This proves that the effects of the catalyst according to the present invention are not a mere addition of the effects of both the metallic components, but correspond to a synergistic effect. In this catalyst, the iron component is contained in a proportion of 5 to 80% by weight as iron oxide to the sum of the zeolite and iron oxide, and the specific metal component is contained in a proportion of 0.1 to 10% by weight to the sum of the zeolite and iron oxide.

The detail of reason is not clear why such effects are derived by adding, to iron, ruthenium or the other specified metal according to the present invention, but it is understood from the above described results that the chemical combination of both the metals is important. Therefore, preparation of the catalyst according to the present invention should be carried out in such a manner that the chemical combination of the both proceeds sufficiently.

A process for the preparation of the catalyst and a conversion process using the same according to the present invention will now be illustrated.

The catalyst of the present invention is generally prepared by mixing intimately a zeolite, preferably a high silica zeolite and an iron-containing Fischer-Tropsch catalyst and then impregnating the mixture with a solution containing at least one metal salt selected from the group consisting of salts of ruthenium, rhodium, platinum, palladium, iridium, cobalt and molybdenum. The intimate mixing is preferably carried out by a gel mixing process or dry mixing process, which will hereinafter be illustrated in detail. The impregnated mixture can be used as a catalyst for the conversion reaction after drying, but it is preferable to calcine it at a temperature of 300°-550° C. for 1-20 hours so as to increase the selectivity of the catalyst. The zeolite used herein is generally a crystalline aluminosilicate in which silica and alumina own jointly oxygen to hold a three-dimensional network structure, the ratio of oxygen atoms to the sum of aluminum atoms and silicon atoms is 2 and the negaive electrovalence of $AlO_4$ tetrahedrons is equilibrated with alkali metal cations, in particular, sodium, potassium or organo nitrogen cations. These zeolites occur often in nature, but can be provided by synthesis. They are characterized by a high adsorption capacity and sometimes are used for the conversion reaction of hydrocarbons, e.g. cracking, isomerization or disproportionation. Generally, the zeolites used for the conversion reaction include erionite, offretite and ferrierite each having a pore diameter of about 5 Å, mordenite and X-zeolite or Y-zeolite of faujasite type each having a pore diameter of about 9 Å, and zeolites of ZSM-5 series having an intermediate pore diameter of 5-9 Å and an $SiO_2$ to $Al_2O_3$ ratio of at least 1, 2. Any zeolites are available for the present invention.

In addition, there can also be used other silicates which have the similar zeolite structure to described above but whose aluminum in the aluminosilicate is partially or completely replaced by trivalent metals such as iron, chromium, vanadium, bismuth, lanthanum, cerium and titanium or by other suitable metals, and which are generally synthesized by a hydrothermal method starting from the corresponding compounds.

The methods of preparing such modified zeolites wherein the aluminum in the aluminosilicate is partially or completely replaced by trivalent metals is well known in the art and will be understood from the following considerations.

A typical zeolite used in the present invention, i.e. ZSM-5 well-known in the art has the following composition expressed as mole ratios of oxides:

$$0.9\pm0.2\ M_{2/n}O.W_2O_3.5-100YO_2.zH_2O$$

wherein M is at least one cation, n is the valence thereof, W is selected from the group consisting of aluminum and gallium, Y is selected from the group consisting of silicon and germanium (Cf. U.S. Pat. No. 3,702,886). That is, even in ZSM-5, it is apparent that gallium is incorporated in the structure of the zeolite in place of aluminum and germanium is used in place of silicon.

Furthermore, of late, various companies, such as Mobil Oil, Shell, UCC and BASF have disclosed zeolites similar to ZSM-5, containing at least one oxide of trivalent metals such as Fe, Cr, V, Bi, La, Ce, Ti, etc. in addition to $SiO_2$, $Al_2O_3$, and oxides of alkali metals and alkaline earth metals. These zeolites can be synthesized by adding the compounds of the trivalent metals prior to the hydrothermal synthesis, which are clearly disclosed in the prior art and represented by the following general formulas:

(1) GB Pat. No. 2,033,358, (Published May 21, 1980)

$$[R_2O,M'_{2/n}O]_w.[Al_2O_3]_x.[SiO_2]_y.[M''_{2/n}O]_z$$

$0.5 < w/x < 3$, $y/x > 20$, $0 < z/x < 100$
R: N— containing cation; M': Group IA metal;
M'': metal selected from the rare earth metals, Cr, V, Mo, In, B, Hg, Te, Ag, Ru, Pt and Pd (2) GB Pat. No. 2,024,790, (Published Jan. 16, 1980)

$$(0.0001\text{ to }1)MnOm.SiO_2$$

M : Cr, Be, Ti, V, Mn, Fe, Co, Zn, Zr, Rh, Ag, Sn, Sb and B (3) Zeolite NU-5 disclosed in U.S. Pat. No. 4,420,467

$$(0.05\text{ to }1.5)R_2O_3.Y_2O_3.\text{at least }10\ XO_2.0\text{ to }2000\ H_2O$$

R : monovalent cation or 1/n of a cation of valency n
X : silicon and/or germanium
Y : one or more of Al, Fe, Cr, V, Mo, As, Mn, Ga and B (4) NL 7,613,952

$$(1.0\pm0.3)R_{2/n}O.[aFe_2O_3.bAl_2O_3].(10-600)SiO_2$$

$$a\geqq0.1, b\geqq0, a+b-1$$

R : one or more cations of one or more valencies
n : Valence of R

Under the situation described in the prior art, it is clear that the zeolite in which a part or all of the aluminum in the zeolite is replaced by other metals can readily be prepared by e.g. the above-described method (1).

For example, a zeolite wherein aluminum is partly replaced or substituted by lanthanum can be prepared by the following method, which is obvious to those skilled in the art from the known methods described above:

Water glass, lanthanum chloride, aluminum chloride and water are mixed so as to give the molar ratio of:

$$36Na_2O.(0.5La_2O_3.0.5Al_2O_3).80SiO_2.160OH_2O$$

After hydrochloric acid is added to the resultant mixture to adjust the pH to 9, propylamine, propyl bromide and methyl ethyl ketone, as organic compounds, are added in a quantity of 20 times the mole number of $(La_2O_3+Al_2O_3)$, mixed well, charged in a stainless auto clave of 500 ml, stirred at about 500 ppm and thus reacted at 160° C. for 3 days. After cooling, the solid product is filtered, washed with water, dried at 110° C. for 1 hour and calcined at 500° C. for three hours to obtain a white and fine crystal material having a chemical composition in terms of moles of oxide under a dehydrated state and exclusive of the organic compound:

$$0.4N_2O.(0.5La_2O_3.0.5Al_2O_3).80SiO_2$$

When the above-described procedure is repeated except that aluminum chloride is not added during the hydrothermal synthesis and water glass, lanthanum chloride and water are mixed to give a mole ratio of:

$$36Na_2O\ La_2O_3.80SiO_2.1600\ H_2O$$

there is obtained the zeolite as used in Example 5 of the present application, which will subsequently describe having a chemical composition in terms of moles of oxides under a dehydrated state and exclusive of the organic compound:

$$0.4Na_2O.La_2O_3.80SiO_2$$

As is evident from the foregoing arguments, a zeolite containing a trivalent metal oxide $Me_2O_3$ can be represented by the general formula:

$$aR_{2/n}O.[bMe_2O_3.cAl_2O_3].(10-600)SiO_2$$

In this formula, b and c have suitable values in the range of $b+c=1$ and depending upon the composition, zeolites with various $Me_2O_3$ to $Al_2O_3$ ratios can be synthesized.

From the above, it is quite apparent that those skilled in the art can readily practice the invention from the known methods in the art as described above.

When using a zeolite having a pore diameter of about 5 Å, the resulting hydrocarbons are linear paraffins, olefins or light hydrocarbons of 5 or less carbon atoms, each having a molecular size of at most about 5 Å and, accordingly, this zeolite is suitable for obtaining lower olefins such as ethylene, propylene, butylene and the like, useful as petrochemical raw materials. In order to increase the yield of gasoline fraction, however, these products should further be subjected to recycling or alkylation in known manner.

When using a zeolite having a pore diameter of at least 9 Å, there are formed not only hydrocarbons of gasoline fraction or less, but also kerosene and gas oil fraction. Thus, this zeolite is used when it is required to produce jointly kerosene and gas oil.

A zeolite having a pore diameter of 5 to 9 Å is the most preferable zeolite for the purpose of obtaining a gasoline fraction in a high yield, typical of which are zeolites of ZSM series developed by Mobil Oil Corp., such as ZSM-5, ZSM-11, ZSM-12, ZSM-21, ZSM-35 and ZSM-38 with a silica to aluminia ratio of at least 12, high silica zeolites consisting of silica-iron-alumina and giving an X-ray diffraction pattern similar to ZSM-5, developed by Shell Internationale Research, ZSM-5 type zeolites obtained by a different production process but having the same X-ray diffraction pattern as ZSM-5, and those in which a part or all of the aluminum is replaced by a trivalent metal. Preparation of the zeolite of this type is preferably carried out by subjecting a silica source, alumina source and alkali source to hydrothermal synthesis in the presence of at least one of organic amines, tetrapropylammonium salts, alcoholamines and diglycolamines and precursors thereof.

The iron-containing Fischer-Tropsch catalyst is precipitated iron or fused iron and is uniformly mixed with the above described zeolite. That is to say, the precipitated iron is ordinarily prepared by adding a precipitant such as ammonia or sodium hydroxide to a solution of an iron salt such as ferric nitrate or ferrous chloride, washing the precipitate and calcining at a temperature of above 300° C. On the other hand, the fused iron is oridinarily prepared by adding a metal oxide as an accelerator to natural magnetite and fusing the mixture, or by fusing high purity cast iron, electrolytic iron or iron carbonyl while blowing oxygen against it to prepare artificial magnetite, to which a metal oxide as an accelerator is added, followed by fusing again. Mixing of the both is generally carried out by a gel mixing process or dry mixing process. The gel mixing process comprises mixing and kneading previously prepared iron oxide hydrated gel with a zeolite powder or suspending a zeolite powder in a solution containing an iron salt such as iron nitrate, chloride, sulfate, carbonate or oxalate, adding an alkali such as aqueous ammonia thereto to precipitate iron oxide and thereby obtaining a uniform mixture of iron and zeolite. The dry mixing process is called "mechanically mixing process", which comprises mixing iron oxide and zeolite powder with grinding to obtain a uniform mixture. Optionally, the preparation of the iron catalyst can be carried out in the presence of copper or potassium in such an amount as used in the ordinary Fischer-Tropsch catalyst. Furthermore, alumina, silica, silica-alumina or their hydrates or natural clays or minerals can be added so as to increase the strength of the catalyst and to improve the moldability of the catalyst as far as the catalytic performance is not deteriorated.

Addition of ruthenium, rhodium, platinum, palladium, iridium, cobalt or molybenum to the zeolite and iron is generally carried out in the form of salts. These metal salts are not particularly limited. However, ruthenium, rhodium, platinum, palladium and iridium are usually added as water-soluble halides or ammine complex salts that are readily available. Particularly, chlorides are preferably used, for example, ruthenium trichloride, rhodium trichloride, chloroplatinic acid, palladium chloride and ammonium hexachloroiridate. Organometal salts such as water-insoluble acetylacetonate salts can also be used. Cobalt is usually added as cobalt nitrate, cobalt chloride, cobalt bromide, cobalt acetate, cobalt carbonate and cobalt sulfate. Molybdenum is preferably addes as ammonium molybdate, but other organo salts such as acetylacetonate salt and tetrapropylmolybdenum can also be used. Addition of ruthenium, rhodium, platinum, palladium, iridium, cobalt and molybdenum can be carried out to any of zeolite, iron and a mixture of zeolite and iron, but it is preferably to support on iron or a mixture of zeolite and iron by impregnation. when ruthenium and other metals are impregnated and supported on a zeolite, a step of grinding and mixing thereafter is required so as to bring iron and ruthenium or other metals into close contact with each other.

A zeolite is generally synthesized in the form containing sodium, potassium or organonitrogen as cation and when using this zeolite for the conversion reaction according to the present invention, at least 50% by weight of the cation is preferably replaced by hydrogen ion, ammonium ion, alkaline earth ions or transition metal ions to increase the acidity using the prior art ion exchange technique comprising treating with an aqueous solution containing a cation to be exchanged. An organonitrogen cation can readily be exchanged with hydrogen ion by heating the zeolite at a temperature of 400° to 700 ° C. to decompose and burn the organonitrogen cation. The proportion of iron and a zeolite in the catalyst is important and generally, the proportion of iron is 5 to 80% by weight as iron oxide to the sum of the zeolite and iron oxide. In addition, ruthenium, rhodium, platinum, palladium, iridium, cobalt and molybdenum are generally supported on a zeolite and iron oxide in a proportion of 0.1 to 101% by weight, preferably 0.3 to 5% by weight as metal to the sum of the zeolite and iron oxide. When such a metal is supported on an iron-containing composition, it is necessary to keep the iron in the form of an iron oxide and, accordingly, in the case of gel mixing a zeolite and iron, a hydrated iron oxide gel is adequately washed with water to remove an impurity of anion from an iron salt used as a raw material, dried and calcined at a temperature of 250° to 550° C. After supporting the metal such as ruthenium, the resulting catalyst after dried can be used for a conversion reaction, but preferably, it is calcined at a temperataure of 300° to 550° C. for 1 to 20 hours for the purpose of increasing the selectivity of the catalyst.

The synthesis gas used a feed gas in the process of the present invention can suitably be prepared by subjecting a carbon source such as coal, natural gas, petroleum coke, shale oil, tar sand or residual oil from petroleum distillation to the prior art gasification technique, e.g. partial oxidation reaction or steam reforming reaction. A precursor of synthesis gas, i.e. mixture of carbon monoxide and steam or mixture of carbon dioxide and hydrogen can also be used as the feed gas. Furthermore, a gaseous mixture containing unreacted gases, obtained by removing liquid hydrocarbons from a fluid discharged out of a reactor for the conversion reaction, can also be used as the feed gas. The mole ratio of hydrogen to carbon monoxide in the synthesis gas, depending upon the variety of a carbon source used as a starting material of gasification, is preferably 0.2 to 6.0 for the present conversion reaction. The conversion reaction according to the present inventon is generally carried out by contacting the synthesis gas with the catalyst at a temperature of 200° to 500° C., preferably 250° to 450° C. under a pressure of 5 to 200 $Kg/cm^2$, preferably 10 to 50 $Kg/cm^2$ at a gas volume hourly space velocity (GHSV) of 250 to 10,000 volumes of gas at the standard temperature and pressure per volume of catalyst. The catalyst can be used in a fixed bed, fluidized bed or suspended bed. In a fixed bed or suspended bed, contacting is preferably carried out in the same contact time as the above described GHSV.

The present invention will be explained in detail with reference to the following examples. It will be obvious to those skill in the art that various changes and modifications can be made in components, ratios, operational orders and the like without departing from the spirit of the present invention. Therefore, the present invention should not be construed as being limited to the following examples.

EXAMPLE 1

A high silica zeolite was prepared by the following procedures. Silica sol, sodium aluminate, caustic soda and water were mixed to give a mole ratio of $10Na_2O.Al_2O_3.46SiO_2.1300H_2O$ to which diglycolamine ($NH_2CH_2CH_2OCH_2CH_2OH_2$) as an organic reagent was added in a quantity of 18 times the moles of alumina with mixing adequately, and the resultant mixture was charged in a 2000 ml stainless autoclave. When the temperature was gradually raised by means of an electric heater and the temperature reached 160° C., the mixture was heated under the spontaneous pressure for 3 days and then allowed to cool naturally. The hydrothermal reaction product was filtered by a glass filter, washed adequately with water until the pH of the washing water became about 8 and dried at 130° C. for 3 hours. Analysis showed that the resulting white fine powder contained 1.8% by weight of sodium and 10.0% by weight of diglycolamine and had a silica to alumina ratio of 27, and X-ray diffraction analysis showed that the product had a diffraction pattern similar to that of ZSM-5 zeolite.

Then, the high silica zeolite was subjected to the following ion exchange treatment to convert into an acid-type zeolite. 500 g of the zeolite was charged with 3000 ml of a 4N aqueous solution of ammonium chloride in a 5000 ml flask, heated gradually and boiled for 3 hours. After cooling, the zeolite was filtered, washed with water, mixed again with a fresh aqueous solution of ammonium chloride and subjected to the same treatment. This operation was carried out three times to exchange the most part of sodium in the zeolite with ammonium ion. After this ion exchange treatment, the zeolite was washed with water to remove the residual ammonium chloride, dried at 130° C. for 3 hours and calcined at 550° C. for 5 hours, whereby to convert the ammonium ion into hydrogen ion, to burn and remove the diglycolamine ion and to convert into hydrogen ion, and to decrease the quantity of the sodium in the zeolite to 0.01% by weight.

Mixing of the zeolite and iron was carried out by the following procedures. 150 g of the above described H-type high silica zeolite powder was added to an aqueous solution containing 759.4 g of ferric nitrate in 2000 ml of water, to which 3N aqueous ammonia was added with adequate agitation until the pH of the solution became 9.0, thus precipitating the iron oxide. The resulting mixture of the zeolite and iron oxide hydrated gel was filtered, washed adequately with water until the washing water was free from nitrate ion, then dried at 130° C. for 3 hours and calcined at 500° C. for 3 hours in a muffle furnace. Chemical analysis showed that the thus resulting composition contained 50% by weight of the zeolite and 50% by weight of the iron oxide.

This composition was then impregnated in conventional manner with an aqueous solution of ruthenium trichloride in a quantity sufficient to give a ruthenium content of 1% by weight, dried at 130° C. and calcined at 500° C. for 3 hours to prepare a ruthenium-containing iron oxide-zeolite catalyst.

Using this catalyst, a synthesis gas conversion reaction was carried out in a microreactor of fixed bed and flow system under the following conditions. 4 ml of the catalyst was charged in the reactor and before the conversion reaction, it was reduced with hydrogen at a temperature of 450° C. under a pressure of 20 $Kg/cm^2G$ for 8 hours and with a synthesis gas at a temperature of 325° C. under 1 atm. for 8 hours. The synthesis gas is mixed gases of $H_2$ and CO with a molar $H_2/CO$ ratio of 2 and the reaction was effected under conditions: reaction temperature 320° C., reaction pressure 20 and 40 $Kg/cm^2G$, GHSV 1,000 $h^{-1}$. The reaction results are shown in Table 1.

The conversion of carbon monoxide in the synthesis gas was 78.1% under a reaction pressure of 40 $Kg/cm^2G$ and 91.2% under a reaction pressure of 20 $Kg/cm^2G$. This catalyst gave a higher conversion efficiency under a lower pressure. The conversion into hydrocarbons reached about 80% while the unfavourable conversion into carbon dioxide was lower, i.e. about 20%. The resultant hydrocarbons were hydrocarbons of at most 10 carbon atoms up to the gasoline boiling point range, which contained a smaller proportion of methane than in the case of using the prior art Fischer-Tropsch synthesis catalyst and a larger proportion of $C_{5+}$ gasoline fraction, amounting to 49.2% under a reaction pressure of 20 $Kg/cm^2G$. According to detailed analysis, the composition of gasoline fraction contained 40% by weight of aromatics, 20% by weight of olefins and 40% by weight of paraffins and had an octane number of 91. This composition was a high quality fuel suitable for use as motor gasoline.

EXAMPLES 2 TO 4

Using ruthenium-supported catalysts having an iron oxide content of 10, 30 and 70% by weight, prepared in an analgous manner to Example 1 except the iron oxide content, the conversion reactions of the synthesis gas were carried out to obtain results as shown in Table 1. The pretreatment of the catalyst and reaction conditions were the same as those of Example 1. The conversion efficiency of CO was increased with the increase of the iron oxide content and substantially constant when the iron oxide content was at least 50% by weight. In an iron oxide content of 10% by weight, the CO conversion was 55%, but the selectivity of CO into hydrocarbons was the highest, i.e. 86.4%. The resulting hydrocarbons contained only about 30% of unfavourable methane, which was not so increased even with the increase of the iron oxide content, and showed a high yield of $C_{5+}$ gasoline fraction as well as a high octane number, about 90.

precipitated iron and ruthenium in a similar manner to Example 1 to prepare a catalyst. This catalyst gave a high CO conversion with decreased formation of $CO_2$ as well as a high yield of gasoline fraction containing much aromatic hydrocarbons and having a high octane number, i.e. 91. Thus, a high quality gasoline was obtained therefrom.

TABLE 1

| | Example 1 | | 2 | 3 | 4 | 5 |
|---|---|---|---|---|---|---|
| Catalyst Component (wt %) | | | | | | |
| Zeolite | 50 | | 90 | 70 | 30 | 50 |
| Iron as $Fe_2O_3$ | 50 | | 10 | 30 | 70 | 50 |
| Ru | 1 | | 1 | 1 | 1 | 1 |
| Reaction Condition | | | | | | |
| Temp. (°C.) | 320 | 320 | 320 | 320 | 320 | 320 |
| Press. (Kg/cm$^2$G) | 20 | 40 | 20 | 20 | 20 | 20 |
| GHSV ($h^{-1}$) | 1,000 | 1,000 | 1,000 | 1,000 | 1,000 | 1,000 |
| CO Conversion (%) | 91.2 | 78.1 | 55.0 | 81.5 | 92.3 | 96.7 |
| Selectivity (%) | | | | | | |
| to $CO_2$ | 20.4 | 16.8 | 13.6 | 21.7 | 26.3 | 22.8 |
| to Hydrocarbons | 79.6 | 83.2 | 86.4 | 78.3 | 73.7 | 77.2 |
| Components of Hydrocarbons (wt %) | | | | | | |
| $C_1$ | 26.2 | 32.3 | 29.3 | 30.2 | 33.1 | 33.5 |
| $C_2$ | 7.7 | 9.6 | 6.3 | 6.9 | 10.5 | 11.2 |
| $C_3$ | 4.5 | 5.2 | 5.6 | 5.0 | 4.6 | 6.8 |
| $C_3$= | 0.7 | 0.7 | 0.3 | 0.6 | 0.6 | 0.3 |
| $C_4$ | 9.8 | 8.8 | 9.9 | 10.9 | 8.7 | 7.8 |
| $C_4$= | 1.9 | 2.2 | 0.5 | 1.0 | 1.5 | 0.7 |
| $C_{5+}$ Gasoline | 49.2 | 41.2 | 48.1 | 45.4 | 40.8 | 39.7 |
| $C_{5+}$ ON F-1 Clear* | 91 | 84 | 92 | 91 | 89 | 91 |

Note:
*Octane Number according to Research Method, "Clear" = lead-free

EXAMPLE 5

Using a catalyst containing 50% by weight of iron oxide and 1% by weight of ruthenium, prepared in an analogous manner to Example 1 using a crystalline lanthanum silicate synthesized by the following procedure instead of the high silica zeolite with a silica to alumina mole ratio of 27, the conversion reaction of the synthesis gas was carried out to obtain results shown in Table 1.

The synthesis method of the crystalline lanthanum silicate is as follows: Water glass, lanthanum chloride, sodium chloride and water were mixed to give a mole ratio of $36Na_2O.La_2O_3.80SiO_2.1600H_2O$, to which hydrochloric acid was added to adjust the pH of the solution to 9 and propylamine and propyl bromide as organic compounds were added in a quantity of 20 times the mole of $La_2O_3$ while mixing adequately, and the resultant mixture was charged in a 1000 ml stainless autoclave. This mixture was thermally treated at 160° C. for 3 days with agitation, cooled, filtered, washed adequately with water until the pH of the washing water be about 8, dried at 110° C. for 12 hours and then calcined at 550° C. for 3 hours. The product had a crystal particle size of about 1 μm and a composition represented by a dehydrated form and omitting the organic compounds:

$$0.4Na_2O.La_2O_3.80SiO_2$$

which was substantially free from aluminum. According to the X-ray diffraction analysis, it was found that the product had a diffraction pattern substantially similar to that of the zeolite synthesized in Example 1 with a high intensity and thus the product was a crystalline lanthanum silicate. This zeolite was immersed in 1N hydrochloric acid at 80° C. for 7 days, washed, filtered, dried at 110° C. for 12 hours, and then combined with

EXAMPLES 6 AND 7

To 2000 ml of an aqueous solution containing 759 g of ferric nitrate was added 5N aqueous ammonia to pH 9 and gelled. The resulting iron oxide hydrated gel was filtered, washed adequately with water until the nitrate ion was hardly detected in the washing water, dried at 130° C. for 5 hours and then calcined at 500° C. for 3 hours in a muffle furnace to form iron oxide.

Example 6: The thus obtained iron oxide powder was mixed adequately with the same H-type high silica zeolite powder as prepared in Example 1, while grinding the both, to which ruthenium trichloride in an amount corresponding to 1.0% by weight of ruthenium was then added. The mixture was allowed to stand for one day, subjected to evaporation, dried and calcined at 500° C. for 3 hours to prepare a catalyst.

Example 7: The thus obtained iron oxide powder was impregnated with ruthenium trichloride in an amount corresponding to 1.0% by weight of ruthenium and then mixed adequately with the same H-type high silica zeolite while grinding the both to prepare another catalyst.

Using these two catalysts differing in preparation process, the conversion reactions of the synthesis gas were carried out in an analogous manner to Example 1, thus obtaining results as shown in Table 2. Any catalysts gave a high CO conversion as well as a high selectivity. It is apparent from these results that even the mechanically mixed iron component and zeolite component give a markedly improved catalytic performance similar to the gel mixing of Example 1.

In this case, addition of ruthenium can be carried out to both the components coexistent, but addition to only the iron component is preferable for raising the selectivity to hydrocarbons and obtaining hydrocarbons enriched with $C_{5+}$ gasoline fraction and with a decreased quantity of methane. It is thus assumed that the improvement of the performance in this catalytic system is mainly due to modification of the iron-containing Fischer-Tropsch catalyst by the addition of the metallic component such as ruthenium.

EXAMPLES 8 TO 10

(Control)

Example 8 uses, as a catalyst, a composition comprising 50% by weight of the H-type high silica zeolite and 50% by weight of iron oxide, prepared in an analogous manner to Example 1 but containing no ruthenium, and Examples 9 and 10 use catalysts consisting of ruthenium supported on the same H-type high silica zeolite, prepared by impregnating in known manner with a solution of ruthenium trichloride in the former case and by ion exchange of ruthenium in known manner using a solution of hexammine ruthenium trichloride in the latter case.

When using the ruthenium-free catalyst of Example 8, the CO conversion was lowered and the yield of hydrocarbons was largely lowered with an increased quantity of $CO_2$. The resultant hydrocarbons contained mainly $C_4$ or lower paraffins, in particular, methane.

On the other hand, when using the iron component-free ruthenium-supported catalyst, there was found no CO conversion activity irrespective of whether calcination of the catalyst was carried out or not in Example 9, while in Example 10, there was found no CO conversion activity in the case of calcining the catalyst at 500° C. for 3 hours, but the non-calcined catalyst gave a higher CO conversion, i.e. 95.2%. However, the resulting hydrocarbons contained 94.5% of methane and $C_{5+}$ gasoline fraction was scarcely recovered.

EXAMPLES 11 TO 17

Using catalysts prepared in an analogous manner to Example 1 except supporting rhodium, platinum, palladium, iridium, cobalt and molybdenum instead of the ruthenium, the conversion reactions of the synthesis gas were carried out to obtain results as shown in Table 3 and 4.

In Example 11, the catalyst containing 1.0% by weight of rhodium supported using rhodium trichloride gave 85.9% by weight of a $C_{5+}$ gasoline fraction having a high octane number, i.e. 89 with a high CO conversion as well as a high selectivity to hydrocarbons.

In Example 12, the catalyst containing 1.0% by weight of ruthenium and 1.0% by weight of rhodium supported using ruthenium trichloride and rhodium trichloride gave a higher selectivity to hydrocarbons and much more improved yield of $C_{5+}$ gasoline fraction than the catalyst free from these metals.

Example 13: Catalyst containing 0.6% by weight of platinum supported using chloroplatinic acid.

Example 14: Catalyst containing 1.0% by weight of palladium supported using palladium chloride.

Example 15: Catalyst containing 0.6% by weight of iridium supported using ammonium hexachloroiridate.

In the conversion reaction of the synthesis gas with an $H_2/CO$ mole ration of 2, any of these catalysts gave a high CO conversion, i.e. at least 80% as well as a high selectivity to hydrocarbons, i.e. at least 77%, the hydrocarbons containing a large proportion of $C_{5+}$ gasoline fraction with a decreased quantity, i.e. about 22% of methane formed and having an octane number of 85 to 89.

It will be understood from these results that supporting of the noble metals on an iron component can give a markedly improved effect in the production of hydrocarbons from the synthesis gas.

In Examples 16 and 17, a catalyst containing 5.0% by weight of cobalt supported using cobalt nitrate and a catalyst containing 5.0% by weight of molybdenum supported using ammonium molybdate were respectively used and gasoline with high octane number was obtained in any case.

TABLE 2

| | Example 6 | 7 | 8 | 9 | 10 |
|---|---|---|---|---|---|
| Catalyst Component (wt %) | | | | | |
| Zeolite | 50 | 50 | 50 | 100 | 100 |
| Iron as $Fe_2O_3$ | 50 | 50 | 50 | 0 | 0 |
| Ru | 1.0 | 1.0 | 0 | 1.0 | 1.0 |
| Reaction Condition | | | | | |
| Temp. (°C.) | 320 | 320 | 320 | 320 | 320 |
| Press. (Kg/cm$^2$G) | 20 | 20 | 20 | 20 | 20 |
| GHSV (h$^{-1}$) | 1,000 | 1,000 | 1,000 | 1,000 | 1,000 |
| CO Conversion (%) | 90.9 | 86.7 | 75.8 | 0 | 95.2 |
| Selectivity (%) | | | | | |
| to $CO_2$ | 26.7 | 21.6 | 41.8 | — | 25.0 |
| to Hydrocarbons | 73.3 | 78.4 | 58.2 | — | 75.0 |
| Components of Hydrocarbons (wt %) | | | | | |
| $C_1$ | 31.2 | 23.6 | 42.6 | — | 94.5 |
| $C_2$ | 7.4 | 5.0 | 7.6 | — | 0.7 |
| $C_3$ | 5.0 | 5.6 | 15.6 | — | 1.0 |
| $C_3^=$ | 0.4 | 0.5 | 0.0 | — | 0.0 |
| $C_4$ | 10.7 | 14.0 | 20.9 | — | 1.1 |
| $C_4^=$ | 0.8 | 1.1 | 0.0 | — | 0.0 |
| $C_{5+}$ Gasoline | 44.5 | 50.2 | 13.3 | — | 2.7 |

TABLE 3

| | Example 11 | 12 | 13 | 14 | 15 |
|---|---|---|---|---|---|
| Catalyst Component (wt %) | | | | | |

TABLE 3-continued

| | Example 11 | 12 | 13 | 14 | 15 |
|---|---|---|---|---|---|
| Zeolite | 50 | 50 | 50 | 50 | 50 |
| Iron as $Fe_2O_3$ | 50 | 50 | 50 | 50 | 50 |
| Metal | 1.0 (Rh) | 1.0 (Rh) 1.0 (Ru) | 0.6 (Pt) | 1.0 (Pd) | 0.6 (Ir) |
| Reaction Condition | | | | | |
| Temp. (°C.) | 350 | 320 | 320 | 320 | 320 |
| Press. (Kg/cm$^2$G) | 40 | 40 | 20 | 20 | 20 |
| GHSV (h$^{-1}$) | 1,000 | 1,000 | 1,000 | 1,000 | 1,000 |
| CO Conversion (%) | 94.0 | 62.4 | 81.1 | 82.4 | 83.9 |
| Selectivity (%) | | | | | |
| to $CO_2$ | 6.5 | 20.4 | 21.7 | 21.4 | 19.3 |
| to Hydrocarbons | 93.5 | 79.6 | 78.3 | 78.6 | 80.7 |
| Components of Hydrocarbons (wt %) | | | | | |
| $C_1$ | 7.1 | 37.3 | 19.6 | 23.9 | 20.6 |
| $C_2$ | 2.9 | 10.5 | 5.3 | 10.9 | 14.9 |
| $C_3$ | 2.5 | 9.1 | 5.0 | 5.3 | 9.3 |
| $C_3^=$ | 0.0 | 0.0 | 0.7 | 0.7 | 0.5 |
| $C_4$ | 1.6 | 7.0 | 13.2 | 10.0 | 10.8 |
| $C_4^=$ | 0.0 | 0.0 | 1.6 | 1.6 | 1.3 |
| $C_{5+}$ Gasoline | 85.9 | 36.1 | 54.6 | 47.6 | 42.6 |
| $C_{5+}$ ON F-1 Clear | 89 | 88 | 86 | 89 | 87 |

EXAMPLE 18

Using a catalyst prepared in an analogous manner to Example 1 except that the crystalline zeolite was an H-type synthesized erionite, the conversion reaction of the synthesis gas with an $H_2/CO$ mole ratio of 2 was carried out to obtain results as shown in Table 4. Under conditions of a temperature 350° C., pressure 20 Kg/cm$^2$G and GHSV 1,000 h$^{-1}$, the CO conversion was 29.2% and the selectivity to hydrocarbons was 65.1%. The proportion of formed methane was less than in the case of using a ruthenium-free catalyst, but the proportion of $C_{5+}$ gasoline fraction was also small, i.e. 13.8% and there were formed large amounts of lower paraffins and olefins of up to $C_2$–$C_4$. This is possible due to that the pore size of the erionite used as one catalyst component is small, that is, about 5 Å and hydrocarbons having a molecular size capable of passing through the pores are selectively formed. Of course, the $C_3$ and $C_4$ fractions containing a large amount of olefins (56%) can readily be converted into gasoline, for example, by alkylation.

EXAMPLE 19

Using a catalyst prepared in an analogous manner to Example 1 except adding to the zeolite of Example 1 alumina sol in a quantity sufficiet to give $Al_2O_3$:$Fe_2O_3$:-zeolite weight ratio of 30:40:30 before precipitating with aqueous ammonia, followed by coprecipitating with iron, the conversion reaction of the synthesis gas was carried out to obtain results as shown in Table 4.

It is evident from the results that the incorporation of alumina serves to improve the activity and selectivity without deteriorating the catalytic performance.

TABLE 4

| | Example 16 | 17 | 18 | 19 |
|---|---|---|---|---|
| Catalyst Component (wt %) | | | | 30 ($Al_2O_3$) |
| Zeolite | 50 | 50 | 50 | 30 |
| Iron as $Fe_2O_3$ | 50 | 50 | 50 | 40 |
| Metal | 5.0 (Co) | 5.0 (Mo) | 1.0 (Ru) | 1.0 (Ru) |
| Reaction Condition | | | | |

TABLE 4-continued

| | Example 16 | 17 | 18 | 19 |
|---|---|---|---|---|
| Temp. (°C.) | 290 | 290 | 350 | 320 |
| Press. (Kg/cm$^2$G) | 40 | 20 | 40 | 20 |
| GHSV (h$^{-1}$) | 1,000 | 1,000 | 1,000 | 1,000 |
| CO Conversion (%) | 91.4 | 75.5 | 29.2 | 78.6 |
| Selectivity (%) | | | | |
| to $CO_2$ | 24.5 | 44.0 | 34.9 | 23.2 |
| to Hydrocarbons | 75.5 | 56.0 | 65.1 | 76.8 |
| Component of Hydrocarbons (wt %) | | | | |
| $C_1$ | 40.4 | 24.1 | 34.7 | 31.3 |
| $C_2$ | 14.0 | 9.0 | 17.4 | 9.6 |
| $C_3$ | 5.3 | 5.9 | 15.0 | 5.1 |
| $C_3^=$ | 0.3 | 0.1 | 4.1 | 1.2 |
| $C_4$ | 5.4 | 8.9 | 5.6 | 11.9 |
| $C_4^=$ | 1.1 | 0.2 | 9.4 | 3.7 |
| $C_{5+}$ Gasoline | 33.5 | 51.8 | 13.8 | 37.2 |
| $C_{5+}$ ON F-1 Clear | 94 | 91 | 82 | 91 |

What is claimed is:

1. A catalyst for the production of hydrocarbons from the synthesis gas, which comprises the combination of an iron-containing Fischer-Tropsch catalyst, a zeolite and at least one metal selected from the group consisting of ruthenium, rhodium, platinum, palladium, iridium, cobalt and molybdenum, said metal being supported upon the iron-containing Fischer-Tropsch catalyst or supported upon a mixture of the iron-containing Fischer-Tropsch catalyst and the zeolite, wherein the iron in terms of iron oxide in the iron-containing Fischer-Tropsch catalyst is present in an amount of 5 to 80% by weight, based on the combined weight of the iron oxide and zeolite, and wherein the metal is present in amounts of 0.3 to 5% by weight, based upon the combined weight of the iron oxide and the zeolite.

2. The catalyst of claim 1, wherein the zeolite is selected from the group consisting of erionite, offretite and ferrierite.

3. The catalyst of claim 1, wherein the zeolite is selected from the group consisting of X-zeolite, Y-zeolite and mordenite.

4. The catalyst of claim 1, wherein the zeolite is selected from the group consisting of zeolites having a pore size of 5 to 9 Å and a silica to alumina mole ratio of at least 12.

5. The catalyst of claim 1, wherein a part of all of the aluminum in the zeolite is replaced by at least one trivalent metal selected from the group consisting of iron, chromium, vanadium, bismuth, lanthanum, cerium and titanium.

6. The catalytic composition of claim 1, wherein the Fischer-Tropsch catalyst is precipitated iron or fused iron.

7. A process for the production of a catalyst, which comprises mixing intimately a high silica zeolite with a Fischer-Tropsch catalyst and then impregnating the mixture with a solution containing at least one metal salt selected from the group consisting of salts of ruthenium, rhodium, platinum, palladium, iridium, cobalt and molybdenum.

8. The process of claim 7, wherein the mixing is carried out by a gel mixing process comprising mixing and kneading previously prepared iron oxide hydrated gel with a zeolite powder.

9. The process of claim 7, wherein the mixing is carried out by a gel mixing process comprising suspending a zeolite powder in a solution containing an iron salt selected from the group consisting of iron nitrate, chloride, sulfate, carbonate and oxalate, adding an alkali thereto to precipitate iron oxide and thus obtaining a uniform mixture of iron and zeolite.

10. The process of claim 7, wherein the mixing is carried out by a dry mixing process comprising mixing and grinding iron oxide and zeolite powder and thus obtaining a uniform mixture of iron and zeolite.

11. The process of claim 7, wherein the impregnated mixture, after dried, is further subjected to calcination at a temperature of 300° to 550° C.

12. The process of claim 7, wherein the high silica zeolite has a silica to alumina mole ratio of at least 12.

13. The process of claim 7, wherein at least one member selected from the group consisting of alumina, silica, silica-alumina and hydrates thereof is further added.

14. The process of claim 9, wherein at least one member selected from the group consisting of alumina, silica, silica-alumina and hydrates thereof is further added before the precipitation of iron oxide.

15. A catalyst produced by the process of claim 11.

* * * * *